United States Patent
Kumar

(10) Patent No.: US 10,332,269 B2
(45) Date of Patent: Jun. 25, 2019

(54) COLOR CORRECTION OF PREVIEW IMAGES FOR PLENOPTIC IMAGING SYSTEMS

(71) Applicant: Aashish Kumar, Bangalore (IN)

(72) Inventor: Aashish Kumar, Bangalore (IN)

(73) Assignee: RICOH COMPANY, LTD., Tokyo (JP)

( * ) Notice: Subject to any disclaimer, the term of this patent is extended or adjusted under 35 U.S.C. 154(b) by 174 days.

(21) Appl. No.: 15/632,221

(22) Filed: Jun. 23, 2017

(65) Prior Publication Data

US 2018/0374229 A1    Dec. 27, 2018

(51) Int. Cl.
| | |
|---|---|
| *H04N 1/60* | (2006.01) |
| *G06T 7/557* | (2017.01) |
| *G02B 3/00* | (2006.01) |
| *G02B 27/00* | (2006.01) |

(52) U.S. Cl.
CPC .......... *G06T 7/557* (2017.01); *H04N 1/6008* (2013.01); *G02B 3/0056* (2013.01); *G02B 27/0075* (2013.01)

(58) Field of Classification Search
CPC ......... G06R 7/557; H04N 1/60; H04N 1/6008
See application file for complete search history.

(56) References Cited

U.S. PATENT DOCUMENTS

| | | | |
|---|---|---|---|
| 8,948,545 B2 | 2/2015 | Akeley et al. | |
| 9,613,417 B2 | 4/2017 | Namboodiri et al. | |
| 10,043,289 B1 | 8/2018 | Rao et al. | |
| 2018/0262734 A1* | 9/2018 | Kumar | H04N 5/23293 |

OTHER PUBLICATIONS

U.S. Appl. No. 15/453,891, filed Mar. 8, 2017, Inventor: Aashish Kumar.

* cited by examiner

*Primary Examiner* — Minh Q Phan
(74) *Attorney, Agent, or Firm* — Fenwick & West LLP

(57) ABSTRACT

In one aspect, a plenoptic imaging system includes imaging optics, a microlens array and a sensor array. A method for color correction of views captured by the plenoptic imaging system includes the following. A plenoptic image of an object captured by the plenoptic imaging system is accessed. The plenoptic image includes many superpixels. Each superpixel includes many subpixels corresponding to different views of the object. The subpixels are of at least two different colors. An initial color view of the object is generated from the plenoptic image. The initial color view includes color pixels. Pixel-wise color correction factors are applied to the color pixels in the initial color view, thereby generating a corrected color view. The pixel-wise color correction factors are determined based on an initial color view generated for a calibration object of known color, as captured by the plenoptic imaging system.

20 Claims, 5 Drawing Sheets
(2 of 5 Drawing Sheet(s) Filed in Color)

COLOR CORRECTION OF PREVIEW IMAGES FOR PLENOPTIC IMAGING SYSTEMS

BACKGROUND

1. Technical Field

This disclosure relates generally to reducing color artifacts in plenoptic imaging systems.

2. Description of the Related Art

Color plenoptic imaging systems have recently received increased attention. They can be used to recalculate a different focus point or point of view of an object in full color, based on digital processing of the captured plenoptic image. The color plenoptic imaging system also finds application in estimating depth to three-dimensional objects that are imaged by the plenoptic imaging system, possibly followed by three-dimensional reconstruction of those objects or the entire three-dimensional scene.

However, image processing of plenoptic imaging systems that include a color sensor array may result in detrimental color artifacts in the reconstructed color images. Typically, these artifacts are caused by differences in sampling between the different color sensors.

SUMMARY

In one aspect, a plenoptic imaging system includes imaging optics, a microlens array and a sensor array. A method for color correction of views captured by the plenoptic imaging system includes the following. A plenoptic image of an object captured by the plenoptic imaging system is accessed. The plenoptic image includes many superpixels. Each superpixel includes many subpixels corresponding to different views of the object. The subpixels are of at least two different colors. An initial color view of the object is generated from the plenoptic image. The initial color view includes color pixels. Pixel-wise color correction factors are applied to the color pixels in the initial color view, thereby generating a corrected color view. The pixel-wise color correction factors are determined based on an initial color view generated for a calibration object of known color, as captured by the plenoptic imaging system.

Other aspects include components, devices, systems, improvements, methods, processes, applications, computer readable mediums, and other technologies related to any of the above.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Embodiments of the disclosure have other advantages and features which will be more readily apparent from the following detailed description and the appended claims, when taken in conjunction with the accompanying drawings, in which:

The figures depict various embodiments for purposes of illustration only. One skilled in the art will readily recognize from the following discussion that alternative embodiments of the structures and methods illustrated herein may be employed without departing from the principles described herein.

DETAILED DESCRIPTION OF THE PREFERRED EMBODIMENTS

The figures and the following description relate to preferred embodiments by way of illustration only. It should be noted that from the following discussion, alternative embodiments of the structures and methods disclosed herein will be readily recognized as viable alternatives that may be employed without departing from the principles of what is claimed.

The present disclosure overcomes the limitations of the prior art by correcting color artifacts in color images, including color previews, generated from the plenoptic images captured by a plenoptic imaging system.

In one aspect, an initial color view is generated from a plenoptic image captured by a plenoptic imaging system of a calibration object of known color. A typical plenoptic imaging system includes a microlens array and a sensor array, and the captured plenoptic image has a structure with superpixels corresponding to the microlenses. The plenoptic imaging system uses a color sensor array, which includes subarrays of different color sensors (e.g., red, green and blue). Accordingly, the captured plenoptic image also has different color channels captured by the different color sensors. For each of the color channels, a center view is generated based on subpixel values at the centroids of the superpixels. The center views are combined into an initial color view of the calibration object. Based on the initial color view, pixel-wise color correction factors are calculated. Typically, the color correction factors are inversely proportional to the pixel values in the initial color view and are stored in a memory unit of the plenoptic imaging system.

Initial color views generated from subsequently captured plenoptic images, can be color corrected based on the color correction factors. This is done on a pixel-by-pixel basis in the color image. Optionally, if the plenoptic imaging system is capturing video, the color correction factors are applied in real-time at a same frame rate as the video capture.

Figure 1:
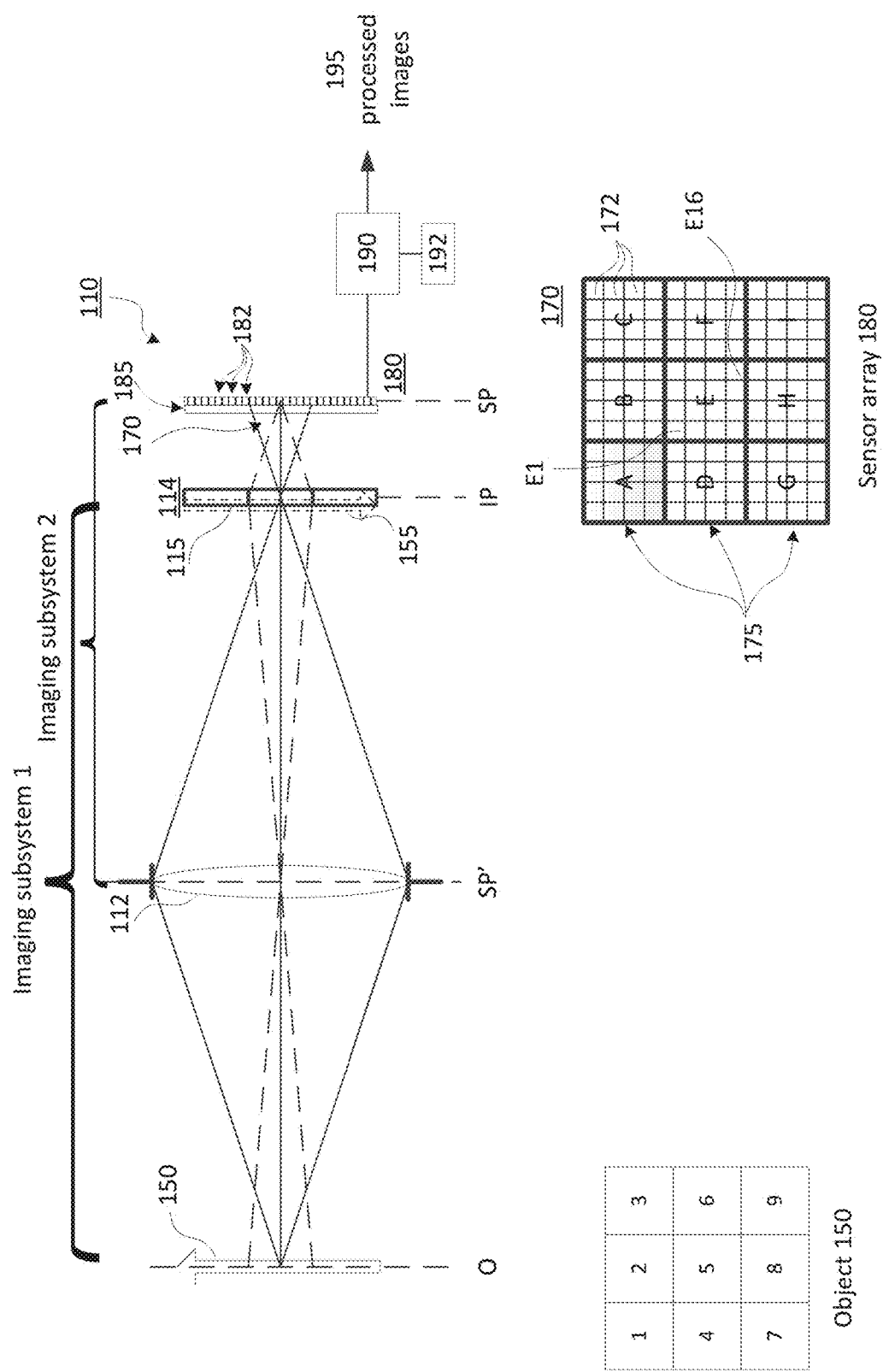
FIG. 1 is a diagram of a plenoptic imaging system, according to one example embodiment.

FIG. 1 is a diagram illustrating a plenoptic imaging system. The plenoptic imaging system 110 includes imaging optics 112 (represented by a single lens in FIG. 1), a microlens array 114 (an array of microlenses 115) and a sensor array 180. The microlens array 114 and sensor array 180 together may be referred to as a plenoptic sensor module. These components form two overlapping imaging subsystems, shown as subsystem 1 and subsystem 2 in FIG. 1.

For convenience, the imaging optics 112 is depicted in FIG. 1 as a single objective lens, but it should be understood that it could contain multiple elements. The objective lens 112 forms an optical image 155 of the object 150 at an image plane IP. The microlens array 114 is located at the image plane IP, and each microlens images the aperture of imaging subsystem 1 onto the sensor array 180. The aperture may be considered the pupil of imaging subsystem 1. That is, the sensor array and aperture are located at conjugate planes SP (i.e., the sensor plane) and SP' (conjugate of the sensor plane). The microlens array 114 can be a rectangular array, hexagonal array or other types of arrays. The sensor array 180 is also shown in FIG. 1.

The sensor array 180 includes different color sensors 182, for example arrays of red, green and blue color sensors arranged in a Bayer pattern. In some embodiments, this is achieved by use of a color filter array 185. In one example embodiment, the color filter array 185 includes red, green and blue microfilters, one per sensor, arranged in a Bayer pattern. The Bayer pattern has twice as many green elements as either red or blue. As a result, the sensor array 180 captures red, green and blue color channels.

The bottom portion of FIG. 1 provides more detail. In this example, the microlens array 114 is a 3×3 array of microlenses 115. The object 150 is divided into a corresponding 3×3 array of regions, which are labeled 1-9. Each of the regions 1-9 is imaged by the imaging optics 112 and imaging subsystem 1 onto one of the microlenses 114. The dashed rays in FIG. 1 show imaging of region 5 onto the corresponding center microlens.

Each microlens 115 images these rays onto a corresponding section of the sensor array 180. The sensor array 180 is shown as a 12×12 rectangular array. FIG. 1 also shows the plenoptic image 170 captured by the sensor array 180, which can be subdivided into superpixels 175, labelled A-I, with each superpixel corresponding to one of the microlenses and therefore also corresponding to a certain region of the object 150. In FIG. 1, superpixel E corresponds to the center microlens, which corresponds to region 5 of the object. That is, the sensors within superpixel E capture light from region 5 of the object.

Each superpixel contains many individual subpixels 172. Generally each subpixel corresponds to a sensor of the sensor array. In this example, the plenoptic image has a 3×3 array of superpixels, and each superpixel 175 has a 4×4 array of individual subpixels 172. Each subpixel within a superpixel captures light from the same region of the object, but at different propagation angles. For example, the upper left subpixel E1 in superpixel E captures light from region 5, as does the lower right subpixel E16 in superpixel E. However, the two subpixels capture light propagating in different directions from the object. This can be seen from the solid rays in FIG. 1. All three solid rays originate from the same object point but are captured by different subpixels within the same superpixel. That is because each solid ray propagates along a different direction from the object.

In other words, the object 150 generates a four-dimensional light field $L(x,y,u,v)$, where L is the amplitude, intensity or other measure of a ray originating from spatial location (x,y) propagating in direction (u,v). Each subpixel 172 captures light from a certain volume of the four-dimensional light field. The subpixels are sampling the four-dimensional light field. The shape or boundary of such volume is determined by the characteristics of the plenoptic imaging system.

In certain plenoptic imaging system designs, the sample volumes are hyperrectangles. That is, every subpixel within a superpixel captures light from the same rectangular (x,y) region associated with the superpixel 175, and each subpixel 172 within the superpixel captures light from a different rectangular (u,v) region. However, this is not always the case. For convenience, the superpixels will be described as capturing light from a certain region of the object 150 (even though subpixels within that superpixel may capture light from slightly different regions), and the subpixels will be described as capturing light from a certain range of propagation directions (even though the range may be different for different subpixels, or even for different (x, y) points captured by the same subpixel). Regardless of the details, the plenoptic imaging system creates a plenoptic image 170, which maps (x,y) spatial locations and (u,v) propagation directions to subpixels. This is in contrast to a conventional image, which maps (x,y) spatial locations to pixels but loses information about the (u,v) propagation directions.

The superpixel is the aggregate of all subpixels that have the same light field viewing region. The view is an analogous concept for propagation direction. The view is the aggregate of all subpixels that have the same light field viewing direction. In the example of FIG. 1, the individual subpixels A1, B1, C1, . . . I1 make up the upper left view of the object. The individual subpixels A16, B16, C16, . . . I16 make up the lower right view of the object. The center view is the view that corresponds to (u,v)=(0,0), assuming that the plenoptic imaging system is an on-axis symmetric system. The centroid of each superpixel is the point in the superpixel that corresponds to (u,v)=(0,0), and the center subpixel is the subpixel that contains that point.

Because the plenoptic image 170 contains information about the four-dimensional light field produced by the object, the processing module 190 can be used to perform different types of analysis, such as depth estimation, three-dimensional reconstruction, synthetic refocusing, extending the depth of focus, spectral analysis and other types of multi-view analysis. The analysis results in processed images 195.

Additionally, the plenoptic imaging system can include a memory unit 192. The memory unit stores plenoptic images and information used by the processing unit 190 (e.g. correction factors) to analyze those plenoptic images. In some embodiments, the memory unit 192 additionally stores processed images 195.

Figure 2:
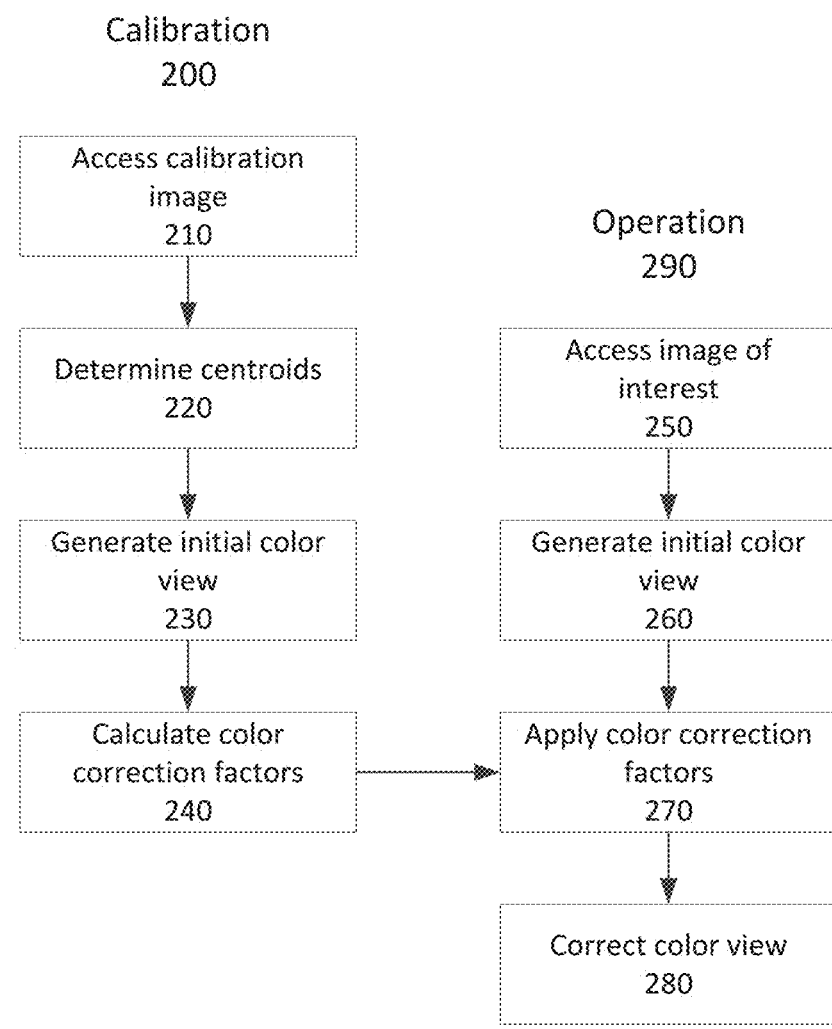
FIG. 2 is a flow diagram of one method for generating a color-corrected view from captured plenoptic images, according to one example embodiment.

In many cases, it is useful to generate a preview image of what the plenoptic image is capturing. However, if the sensor array is a color array, these preview images may suffer from color artifacts. FIG. 2 is a flow diagram of one method for the color correction of color views captured by a plenoptic imaging system. This process is explained with reference to FIGS. 3-5. The process includes two phases: a calibration phase 200 and an operational phase 290. In the calibration phase 200, color correction factors are calculated based on plenoptic imaging of a calibration object of known color. In the operational phase 290, plenoptic images of objects are captured and the resulting color views are corrected on a pixel-by-pixel basis using the color correction factors from the calibration phase 200.

In the example described below, both processes 200 and 290 of FIG. 2 are performed by the plenoptic imaging system (e.g., via the processing module 190). In another embodiment, one or both processes are performed by a computing system separate from the plenoptic imaging system. Other modules may perform some or all of the steps of the process in other embodiments. Likewise, embodiments may include different and/or additional steps, or perform the steps in different orders.

Consider first the calibration process 200, which is explained below with reference to FIG. 3. To begin, the processing module 190 accesses 210 a plenoptic image 170 captured by the plenoptic imaging system of a calibration object of known color. In some embodiments, the calibration object is a uniformly illuminated white object (e.g., a white card that when imaged fills the sensor array 180). This plenoptic image will be called the calibration image. More generally, the calibration object preferably is uniformly lit and does not include characteristics (e.g. patterns, features or other high frequency content) that can create optical discrepancies in the captured plenoptic image. In some embodiments, the calibration image can be a combination of plenoptic images capturing the calibration object at several distances and/or orientation angles. For example, the calibration object can be imaged at 1 m, 2 m, or 5 m, etc., and/or the calibration object can be imaged from the front (e.g. 0°), the front right (e.g. 45°), the front-left (e.g. −45°), etc.

Figure 3:
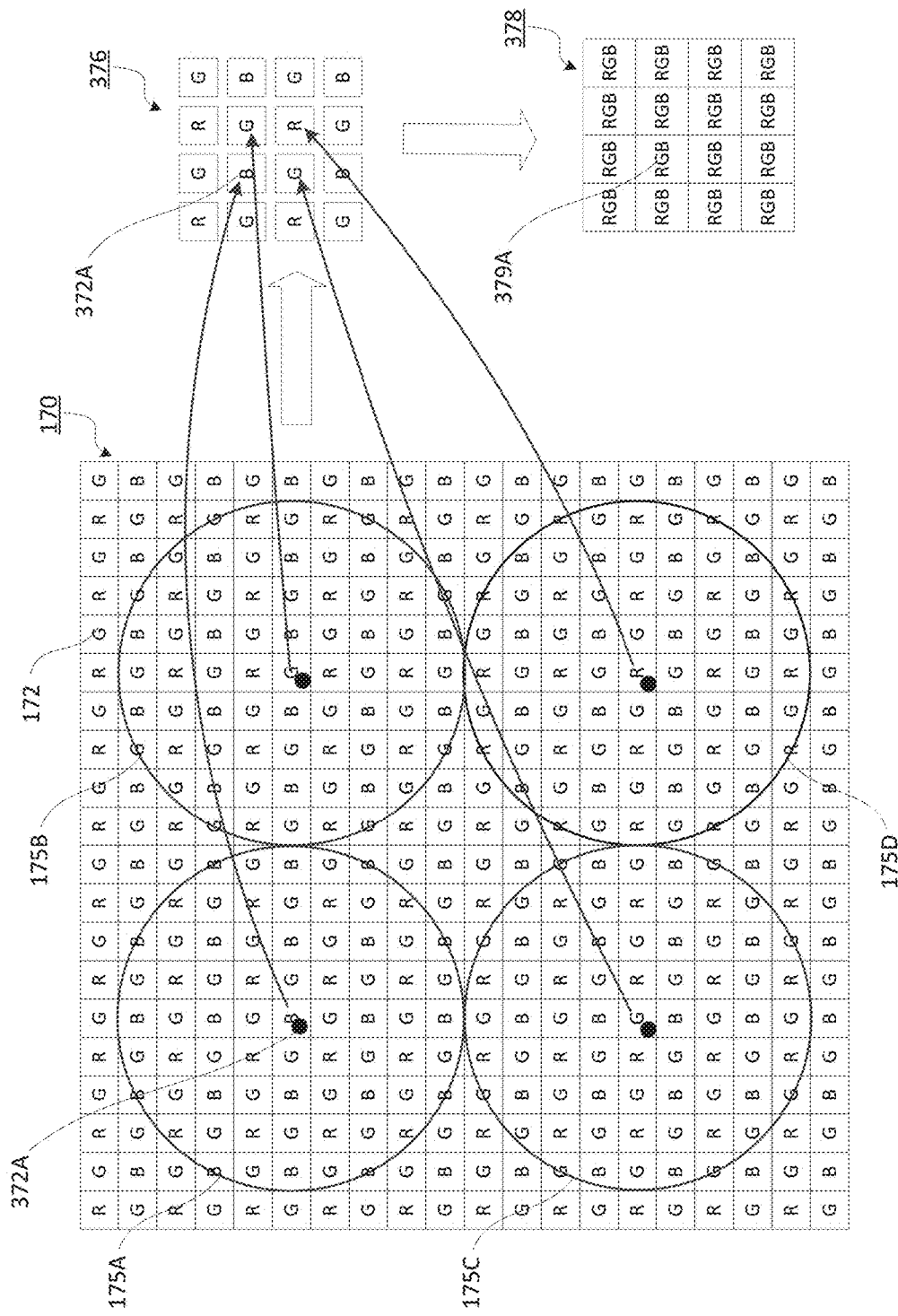
FIG. 3 is a diagram illustrating the method of FIG. 2, according to one example embodiment.

The lefthand side of FIG. 3 shows a portion of a plenoptic image 170 that contains a 2×2 array of superpixels 175A-D. The full plenoptic image will be much larger and contain many more superpixels. In FIG. 3, these superpixels 175 are largely circular, as opposed to the square superpixels shown in FIG. 1, because the pupil for the primary optics 112 is round. Additionally, these superpixels 175 are square packed because the microlens array 114 is a square array. In other embodiments, the superpixels can have different shapes and the array of superpixels can take any other packing structure (e.g. rectangular or hexagonal). Each small square is a subpixel 172 of the plenoptic image. In this example, a Bayer filter is used so the subpixels 172 are red, green or blue color subpixels, as denoted by the R, G or B in each square.

The processing module 190 determines 220 the centroids of the superpixels of the calibration image. The centroid is location in the superpixel that corresponds to the (0,0) view. The centroids can be determined 220 using a signal power analysis, a geometric analysis, or spectral analysis of each superpixel, for example. In FIG. 3, the centroid of each superpixel 175A-D is marked by a "•", and the center subpixel 372A-D is the subpixel with the "•". For clarity, only center subpixel 372A is labelled in FIG. 3. The center subpixel 372 of each superpixel 175 is the subpixel that corresponds to the center view of the plenoptic image.

The upper right of FIG. 3 shows a collection of just the center subpixels 372. For convenience, this collection of center subpixels will be referred to as the captured center view data 376. Only a 4×4 set of center subpixels is shown. The full collection will have the same number of center subpixels as there are superpixels. The center 2×2 set of center subpixels in this captured data 376 are the center subpixels 372A-D from the plenoptic image 170. The arrows between the plenoptic image 170 and the captured data 376 show the correspondence. Center subpixel 372A from the plenoptic image 170 corresponds to center subpixel 372A in the captured center view data 376, and so on.

Returning to FIG. 2, the processing module 190 generates 230 a color preview image 378. For reasons that will be apparent, this color image 378 will be referred to as an initial color view. It is initial in the sense that it is before color correction. It is a view in the sense that it typically is from one viewpoint (e.g., the center view). In other embodiments, views other than the center view can be chosen to generate a preview image. The preview image can also be based on a multiple number of views. When the object is a calibration object, for convenience, this initial color view will be called the initial calibration view.

An initial color view includes different color components because it is a color image. However, as shown in FIG. 3, each center subpixel 372 in the captured data 376 is a specific color. The other color components typically are interpolated from other data. For example, in FIG. 3, center subpixel 372A is a blue subpixel. The red and green components for that location are interpolated from neighboring red and green values. In one approach, bilinear interpolation is used. This provides red, green and blue components for the color pixel 379A, rather than just the blue component of center subpixel 372A. In this way, each color pixel 379 of the initial color view 378 (i.e., each individual square in FIG. 3) has red, green and blue color components.

In one approach, the initial color view is generated 230 as follows. The center view for a principal color (e.g. green because it has twice as many pixels in a Bayer pattern) is generated via bilinear interpolation about each centroid. Color ratios for the non-principal color channels (e.g. blue, red) are calculated using a synthetic aperture within each superpixel. The center view for non-principal colors is then generated based on the center view of the principal color and the color ratios between the principal and non-principal colors. Typically, the principal color is the color which has the highest resolution (i.e. largest number of sensors) in the sensor array (e.g. green for a Bayer sensor).

As a numerical example, assume that the green component for a color pixel (7,5) is determined to be 0.64 using bilinear interpolation. The red-to-green color ratio for the superpixel is calculated as 1.34 and the blue-to-green color ratio is calculated as 0.94. Using the color ratios, red value at the centroid is calculated as 0.64×1.34=0.86 and the blue value at the centroid as 0.64×0.94=0.60. This yields a color pixel 379 with the RGB components (0.86, 0.64, 0.60) for this superpixel. The processing module similarly generates a color pixel 379 for all superpixels to generate 230 the initial color view.

Figure 4:
FIG. 4 illustrates an initial color view of a white calibration object, according to one example embodiment.

FIG. 4 is an initial color view generated 230 from a calibration image for a plenoptic otoscope, according to one example embodiment. In this example, the plenoptic otoscope captures plenoptic images of a calibration object at different distances and orientation angles to create a calibration image. The calibration image is processed as described above to generate the initial calibration view shown in FIG. 4. Color artifacts are evident as red and blue striations throughout the image.

Returning to FIG. 2, the processing module 190 calculates 240 color correction factors for each color pixel 379 of the initial calibration view. Since the calibration object is controlled and of known color, the ground truth values for the color pixels 379 are known and color correction factors can be calculated based on the difference between the actual and ideal values. In some embodiments, a separate color correction factor is calculated for each color channel of the color pixels.

Typically, the calibration object is a constant color and generates a preview image that should also be a constant color. In that case, if the color correction factors are multiplicative for each color pixel, then the pixel-wise color correction factors for each color channel are inversely proportional to the values of the color pixels of the initial calibration view. That is, the pixel-wise color correction factors $$C(i,j,\lambda) = k(\lambda)/P(i,j,\lambda) \qquad (1)$$

where $C(i,j,\lambda)$ is the color correction factor for color component X of color pixel $(i,j)$, $P(i,j,\lambda)$ is the observed value of color component X of color pixel $(i,j)$, and $k(\lambda)$ is a constant that may be different for each color channel.

Continuing the above example, the color pixel at location (7,5) of the initial calibration view has the components (0.86, 0.64, 0.60). The calibration object is white and should produce a color pixel of (1, 1, 1). The processing module calculates a color correction factor for that color pixel of 1/0.86=1.16 for the red channel, 1/0.64=1.56 for the green channel, and 1/0.60=1.66 for the blue channel. The same calculation can be made for other color pixels, yielding pixel-wise color correction factors. In other embodiments, the color correction factors can be determined using component scaling, the Von Kries method, the modified Von Kries method, the Jameson-Hurvich induced opponent theory, or any other color scaling methods.

The processing module 190 can store color correction factors for future use by the plenoptic imaging system. The correction factors can be stored on a memory storage unit of the plenoptic imaging system (e.g. a solid state memory). In other embodiments, the correction factors can be stored on a memory system accessible by the plenoptic imaging system (e.g. a coupled computer system). Similarly, the plenoptic imaging system can store any information associated with the color correction process including the centroid locations, the calculated pixel values for any color pixel of the calibration image, center views for each color channel of the calibration image, initial color views of the calibration image, etc.

In some embodiments, accessing 210 a calibration image, determining 220 the centroids of the calibration image, generating 230 an initial color view, and calculating 240 pixel-wise color correction factors can occur before standard operational use of the plenoptic imaging system.

Now consider the operation process 290 of FIG. 2. In normal operation, the plenoptic imaging system captures plenoptic images of objects of interest, rather than of calibration objects. For example, a plenoptic otoscope could be capturing plenoptic images of a patient's ear canal. The plenoptic imaging system accesses 250 a plenoptic image of an object of interest. For convenience, the plenoptic image will be called the raw image. After this, the processing module 190 generates 260 an initial color view for the raw image. Typically, the process 230 that is used to generate the initial color view of the calibration object will also be used to generate 260 the initial color view of a real object of interest. In the operation process 290, the step of determining centroids 220 is not expressly shown because often the centroid locations will be known rather than determined.

Continuing in FIG. 2, the processing module 190 applies 270 the pixel-wise color correction factors to the raw image initial view to generate 280 a corrected color view. One approach includes a pixelwise multiplication of the color correction factors and the color pixels. A pixelwise multiplication is the multiplication of a correction factor at a pixel location by the pixel value of the initial color view at the same pixel location. In some embodiments, different color correction factors are applied to each color channel. Further, in some embodiments, the processing module accesses the color correction factors from the memory storage unit of the plenoptic imaging system.

Continuing the example from above, the processing module calculates the corrected color view with a pixelwise multiplication of the color correction factors and the initial color view. That is $$P_{corr}(i,j,\lambda)=C(i,j,\lambda)P_{init}(i,j,\lambda) \quad (2)$$

where $P_{corr}(i,j,\lambda)$ are the corrected pixel values, $C(i,j,\lambda)$ are the pixel-wise color correction factors, $P_{init}(i,j,\lambda)$ are the initial pixel values, and $(i,j,\lambda)$ are indices for the color pixel and the color component.

Using the numbers from above, the processing module accesses the color correction factors from a memory unit of the plenoptic imaging system. The color correction factors for color pixel (7,5) are (1.16, 1.56, 1.66). The color pixel (7,5) from the initial color view has values (0.34, 0.18, 0.56). The processing module uses a pixelwise multiplication and calculates a corrected pixel value of 1.16×0.34=0.39 for the red channel, 1.56×0.18=0.28 for the green channel, and 1.66×0.93=0.93 for the blue channel. The processing module generates a color pixel for the corrected color view at the pixel location (7,5) with the RGB components (0.34, 0.28, 0.93). In some embodiments, the processing module can further modify the corrected color pixel values (e.g. clipping the pixel value 1.16 to 1.00). The processing module similarly generates a corrected color pixel for all pixel locations to create a corrected color view.

Figure 5A:
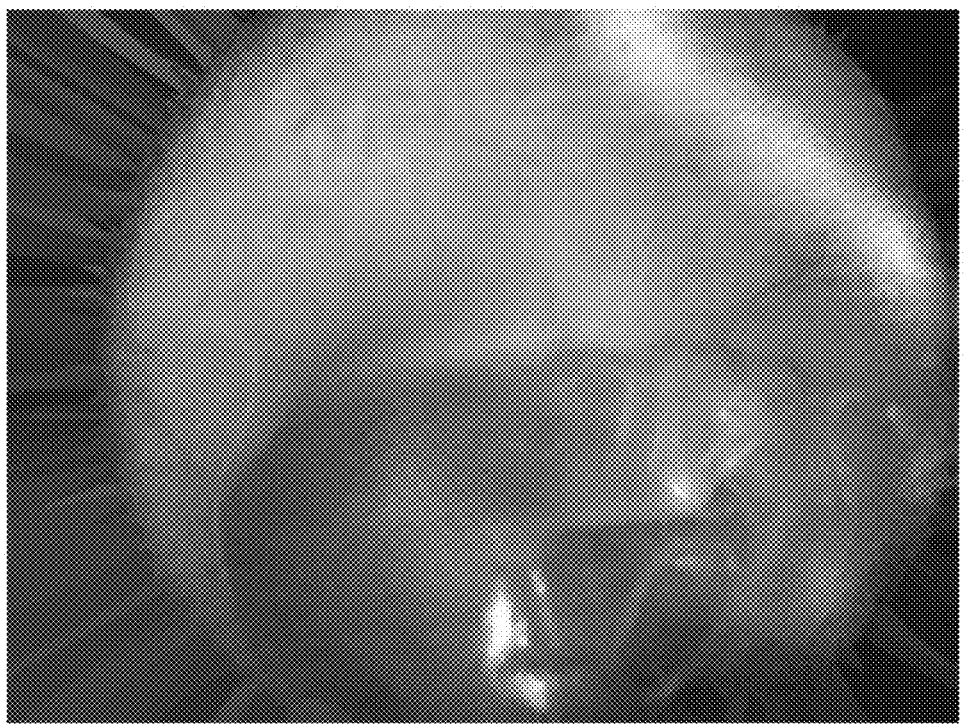
FIGS. 5A and 5B illustrate an initial color view and a corrected color view of a human inner ear, according to one example embodiment.
Figure 5B:
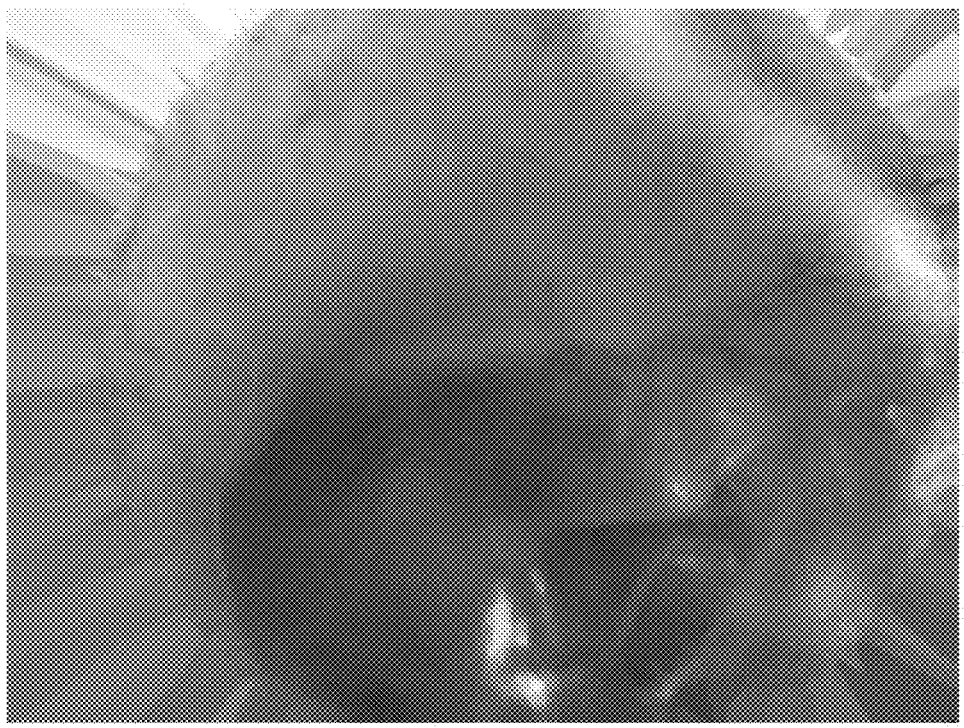

For example, FIGS. 5A and 5B are an initial color view and a corrected color view for a plenoptic otoscope, according to one example embodiment. In these examples, a plenoptic otoscope captures plenoptic images of the interior of the ear. The captured plenoptic images are processed as described above to generate initial color views. FIG. 5A is the initial color view before the color correction factors are applied. Color artifacts are evident as lines of red and blue across the image. FIG. 5B is the corrected color view after application of pixel-wise color correction factors. The color artifacts have been largely reduced.

The initial color views and color correction factors described in the above examples are expressed as the red, green and blue components at each pixel location. In alternate embodiments, the initial color views and/or color correction factors can be based on other image data determined from the plenoptic image. For example, the system may determine a brightness, chrominance, luminance, hue, etc. and generate initial color views and/or pixel-wise correction factors for these values. Additionally, a similar correction process can be applied to a plenoptic imaging system with a monochromatic sensor array 180. That is, the system can generate initial calibration views, calculate correction factors, generate raw image initial views, and apply the correction factors to reduce monochromatic image artifacts.

In some cases, the plenoptic imaging system is capturing video. That is, plenoptic images are captured at video rate. Preferably, the plenoptic imaging system captures raw plenoptic images, processes the views, and creates a corrected view such that the corrected views are created at the same frame rate as the capture of the plenoptic video. If the imaging system is capturing 15 or more frames per second, then the processing module has 66 ms or less to create the corrected view frame for real-time operation. The corrected views provide a real-time preview of what the plenoptic imaging system is capturing.

For a plenoptic otoscope, the real-time video allows the physician to guide the otoscope to capture images of the eardrum or other relevant anatomical features. For example, a plenoptic imaging system used as an otoscope in a medical procedure may have the following specifications: a microlens size of 55 μm, a sensor array size of 3376×2704 pixels (i.e. 9 Mega pixels), an individual pixel size of 3.7 μm, and a frame rate for the preview video of 15-18 frames per second. These are just an example. Other embodiments may have different specifications.

Generally, the preview images (i.e. frames of the preview video) have a resolution that does not exceed the number of microlenses in the microlens array, which is significantly less than the total number of sensors in the sensor array. However, in some embodiments, various methods can be used to increase the resolution of the images above the number of microlenses in the array. Some examples include super-resolution, sub-sensor sampling, interpolation, resampling, box sampling, and vectorization.

Although the detailed description contains many specifics, these should not be construed as limiting the scope of the invention but merely as illustrating different examples and aspects of the invention. It should be appreciated that the scope of the invention includes other embodiments not discussed in detail above. Various other modifications, changes and variations which will be apparent to those skilled in the art may be made in the arrangement, operation and details of the method and apparatus of the present invention disclosed herein without departing from the spirit and scope of the invention as defined in the appended claims. Therefore, the scope of the invention should be determined by the appended claims and their legal equivalents.

In alternate embodiments, aspects of the invention are implemented in computer hardware, firmware, software, and/or combinations thereof. Apparatus of the invention can be implemented in a computer program product tangibly embodied in a machine-readable storage device for execution by a programmable processor; and method steps of the invention can be performed by a programmable processor executing a program of instructions to perform functions of the invention by operating on input data and generating output. The invention can be implemented advantageously in one or more computer programs that are executable on a programmable system including at least one programmable processor coupled to receive data and instructions from, and to transmit data and instructions to, a data storage system, at least one input device, and at least one output device. Each computer program can be implemented in a high-level procedural or object-oriented programming language, or in assembly or machine language if desired; and in any case, the language can be a compiled or interpreted language. Suitable processors include, by way of example, both general and special purpose microprocessors. Generally, a processor will receive instructions and data from a read-only memory and/or a random access memory. Generally, a computer will include one or more mass storage devices for storing data files; such devices include magnetic disks, such as internal hard disks and removable disks; magneto-optical disks; and optical disks. Storage devices suitable for tangibly embodying computer program instructions and data include all forms of non-volatile memory, including by way of example semiconductor memory devices, such as EPROM, EEPROM, and flash memory devices; magnetic disks such as internal hard disks and removable disks; magneto-optical disks; and CD-ROM disks. Any of the foregoing can be supplemented by, or incorporated in, ASICs (application-specific integrated circuits) and other forms of hardware.

What is claimed is:

1. For a plenoptic imaging system comprising imaging optics, a microlens array and a sensor array, a method for color correction of views captured by the plenoptic imaging system, comprising:
   accessing a plenoptic image of an object captured by the plenoptic imaging system, the plenoptic image comprising a plurality of superpixels, each superpixel comprising subpixels corresponding to different views of the object, the subpixels comprising subpixels of at least two different colors;
   generating an initial color view of the object from the plenoptic image, the initial color view comprising a plurality of color pixels; and
   applying pixel-wise color correction factors to the color pixels in the initial color view, thereby generating a corrected color view, the pixel-wise color correction factors determined based on an initial color view generated for a calibration object of known color captured by the plenoptic imaging system.

2. The method of claim 1 wherein applying pixel-wise color correction factors to the color pixels comprises multiplying the color pixels times the pixel-wise color correction factors.

3. The method of claim 2 wherein the pixel-wise color correction factors are inversely proportional to pixel values of the initial color view generated for the calibration object.

4. The method of claim 1 wherein the color pixels comprise different color channels, and applying pixel-wise color correction factors to the color pixels comprises applying different pixel-wise color correction factors to the different color channels.

5. The method of claim 1 wherein the color pixels comprise a chrominance channel, and applying pixel-wise color correction factors to the color pixels comprises applying the pixel-wise color correction factors to the chrominance channel.

6. The method of claim 1 wherein the pixel-wise color correction factors are determined as part of a calibration process of the plenoptic imaging system.

7. The method of claim 1 wherein the pixel-wise color correction factors are determined based on initial color views generated for the calibration object at a plurality of distances and a plurality of orientation angles.

8. The method of claim 1 further comprising:
   the plenoptic imaging system capturing a plenoptic image of the calibration object of known color;
   generating an initial color view of the calibration object from the plenoptic image of the calibration object; and
   calculating the pixel-wise color correction factors based on differences between the initial color view of the calibration object and the known color of the calibration object.

9. The method of claim 1 wherein the corrected color view provides a preview of what the plenoptic imaging system is capturing.

10. The method of claim 9 wherein the plenoptic imaging system captures plenoptic video comprising frames of plenoptic images, the method for color correction is applied to the frames of plenoptic images, and the corrected color views are created at a same frame rate as the capture of the plenoptic video.

11. The method of claim 9 wherein the plenoptic imaging system captures plenoptic video comprising frames of plenoptic images, the method for color correction is applied to the frames of plenoptic images, and the corrected color views provide a real-time preview of what the plenoptic imaging system is capturing.

12. The method of claim 1 wherein the initial color view of the object comprises not more than one color pixel per superpixel in the plenoptic image.

13. The method of claim 1 wherein the initial color view of the object is a center view of the object.

14. The method of claim 13 further comprising:
   determining centroids for the superpixels, wherein generating the initial color view of the object from the plenoptic image is based on subpixels located at the centroids of the superpixels.

15. The method of claim 1 wherein the method for color correction is applied to multiple views of the object generated from the plenoptic image.

16. A plenoptic imaging system comprising:
- imaging optics that image an object onto an image plane of the imaging optics, the imaging optics characterized by a pupil located at a pupil plane;
- a microlens array located at the image plane of the imaging optics; and
- a sensor array located at a conjugate to the pupil plane, the microlens array imaging the pupil plane onto the sensor array, the sensor array capturing a plenoptic image of the object, the plenoptic image comprising a plurality of superpixels, each superpixel comprising subpixels corresponding to different views of the object, the subpixels comprising subpixels of at least two different colors; and
- a processing module that:
  - generates an initial color view of the object from the plenoptic image, the initial color view comprising a plurality of color pixels; and
  - applies pixel-wise color correction factors to the color pixels in the initial color view, thereby generating a corrected color view, the pixel-wise color correction factors determined based on an initial color view generated for a calibration object of known color captured by the plenoptic imaging system.

17. The plenoptic imaging system of claim 16 further comprising:
- a memory unit storing the pixel-wise color correction factors.

18. The plenoptic imaging system of claim 16 wherein the plenoptic imaging system captures plenoptic video comprising frames of plenoptic images, the processing module generates the initial color view and applies pixel-wise color correction factors to the frames of plenoptic images, and the corrected color views provide a real-time preview of what the plenoptic imaging system is capturing.

19. The plenoptic imaging system of claim 16 wherein the plenoptic imaging system is a plenoptic otoscope.

20. A non-transitory computer-readable storage medium storing executable computer program instructions for color correction of views captured by a plenoptic imaging system, the instructions executable by a processor and causing the processor to perform a method comprising:
- accessing a plenoptic image of an object captured by the plenoptic imaging system, the plenoptic image comprising a plurality of superpixels, each superpixel comprising subpixels corresponding to different views of the object, the subpixels comprising subpixels of at least two different colors;
- generating an initial color view of the object from the plenoptic image, the initial color view comprising a plurality of color pixels; and
- applying pixel-wise color correction factors to the color pixels in the initial color view, thereby generating a corrected color view, the pixel-wise color correction factors determined based on an initial color view generated for a calibration object of known color captured by the plenoptic imaging system.

* * * * *